US006166305A

United States Patent [19]
Martino

[11] Patent Number: 6,166,305
[45] Date of Patent: Dec. 26, 2000

[54] INBRED SUNFLOWER LINE PHA207

[75] Inventor: Carlos Martino, Venado Tuerto, Argentina

[73] Assignee: Pioneer Hi-Bred International, Inc., Des Moines, Iowa

[21] Appl. No.: 09/056,303

[22] Filed: Apr. 7, 1998

[51] Int. Cl.⁷ .............................. A01H 5/00; A01H 1/04; A01H 5/10; C12N 5/04

[52] U.S. Cl. ........................ 800/322; 800/260; 800/298; 435/428

[58] Field of Search ...................................... 800/322, 298, 800/260, 274; 435/428, 430, 430.1

[56] References Cited

U.S. PATENT DOCUMENTS

B1 4,627,197  12/1986  Fick .
B1 4,743,402   5/1988  Fick .

OTHER PUBLICATIONS

Soldatov, K.I., "High–Oleic Variety of Sunflower, Selection, Growing of Seeds and Technology of Cultivation of Technical Crops", Moscow, Kolos, 1980, pp. 35–42.

Soldatov, K.I., "Chemical Mutagenesis in Sunflower Breeding", 7th Int. Sunflower Conf., pp. 352–357, 1976.

Stafford, et al. Registration of sunflower parental line HA 207. Crop Science. vol. 23, No. 1, p. 195, 1993.

*Primary Examiner*—Gary Benzion
*Assistant Examiner*—Melissa L. Kimball
*Attorney, Agent, or Firm*—Pioneer Hi-Bred International, Inc.

[57] ABSTRACT

An inbred sunflower line, designated PHA207, the plants and seeds of inbred sunflower line PHA207, methods for producing a sunflower plant produced by crossing the inbred line PHA207 with itself or with another sunflower plant, and hybrid sunflower seeds and plants produced by crossing the inbred line PHA207 with another sunflower line or plant.

11 Claims, No Drawings

INBRED SUNFLOWER LINE PHA207

FIELD OF THE INVENTION

This invention is in the field of sunflower breeding, specifically relating to an inbred sunflower line designated PHA207.

BACKGROUND OF THE INVENTION

The goal of plant breeding is to combine in a single variety or hybrid various desirable traits. Major objectives in sunflower breeding include improved seed yield, earlier maturity, shorter plant height, uniformity of plant type, and disease and insect resistance. High oil percentage is important in breeding oilseed types whereas large seed size, a high kernel-to-hull ratio, and uniformity in seed size, shape, and color are important objectives in breeding and selection of nonoilseed sunflower. Other characteristics such as improved oil quality, protein percentage and protein quality are also important breeding objectives.

Sunflower are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Sunflower (*Helianthus annuus* L.), can be bred by both self-pollination and cross-pollination techniques. The sunflower head (inflorescence) usually is composed of about 1,000 to 2,000 individual disk flowers joined to a common base (receptacle). The flowers around the circumference are ligulate ray flowers with neither stamens nor pistil. The remaining flowers are hermaphroditic and protandrous disk flowers.

Natural pollination of sunflower occurs when flowering starts with the appearance of a tube partly exserted from the sympetalous corolla. The tube is formed by the five syngenesious anthers, and pollen is released on the inner surface of the tube. The style lengthens rapidly and forces the stigma through the tube. The two lobes of the stigma open outward and are receptive to pollen but out of reach of their own pollen initially. Although this largely prevents self-pollination of individual flowers, flowers are exposed to pollen from other flowers on the same head by insects, wind, and gravity.

A reliable method of controlling male fertility in plants offers the opportunity for improved plant breeding. This is especially true for development of sunflower hybrids, which relies upon some sort of male sterility system. Two types of male sterility, genetic and cytoplasmic, have been found in sunflower.

Hybrid sunflower seed is typically produced by a male sterility system incorporating genetic or cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in sunflower plants, since only the female provides cytoplasm to the fertilized seed. CMS plants are fertilized with pollen from another inbred that is not male-sterile. Pollen from the second inbred may or may not contribute genes that make the hybrid plants male-fertile.

Plant breeding methods involving genetic or cytoplasmic male sterility, or induction of male sterility by gibberellic acid, allow for complete hybridization of lines and hence greater precision in estimating combining ability. Various tester parents and tester schemes are being used. A. V. Anaschenko has conducted extensive testing for general combining ability by the top cross method with chemical emasculation of the female parent with gibberellic acid. He has used open pollinated cultivars, hybrids, and inbred lines as testers. A. V. Anaschenko, *The Initial Material for Sunflower Heterosis Breeding*, Proceedings of the 6th International Sunflower Conference, 391–393 (1974). B. Vranceanu used a monogenic male sterile line as a female parent to test for general combining ability and subsequent diallel cross analysis with artificial emasculation to test for specific combining ability. B. Vranceanu, *Advances in Sunflower Breeding in Romania*, Poc. 4th International Sunflower Conference (Memphis, Tenn.), 136–146 (1970). Recent testing by breeders in the United States has included the rapid conversion of lines to cytoplasmic male sterility by using greenhouses and winter nurseries and subsequent hybrid seed production in isolated crossing blocks using open pollinated cultivars, synthetics, composites, or inbred lines as tester.

There are several methods of conferring genetic male sterility available, such as multiple mutant genes at separate locations within the genome that confer male sterility. According to A. 1. Gundaev, *Prospects of Selection in Sunflower for Heterosis*, Sb. Rab. Maslichn. Kult., 3:15–21 (1966), genetic male sterility first was reported in the Soviet Union by Kuptsov in 1934. Since then, numerous investigators have reported genetic male sterility in sunflower. Vranceanu indicated isolation of more than thirty sources of male sterility in the Romanian program, most of which were controlled by a single recessive gene. Diallel cross analysis of ten of these lines indicated the presence of five different genes. The studies of E.D. Putt and C.B. Heiser were some of the first reported to assess the value of genetic male sterility to produce hybrid seed. They concluded that lines of partial male sterility may have the most immediate value in commercial production of hybrid seed as not only could the partial male sterile lines hybridize well in crossing plots, they could also be increased and easily maintained. E. D. Putt and C. B. Heiser, Jr., *Male Sterility and Partial Male Sterility in Sunflowers*, Crop Science, 6:165–168 (1966).

In order to produce hybrid seed using complete genetic male sterility, the male sterile locus must be maintained in the heterozygous condition in the female parent. This is accomplished by sib pollinations of male sterile plants (ms ms) with heterozygous male fertile plants (Ms ms) within the female parent. The resultant progeny from the male sterile plants will segregate 1:1 for fertile and sterile plants. When such lines are used in hybrid seed production the fertile plants must be removed prior to flowering to obtain 100% hybridization with the male parent line.

Production of hybrid seed by the genetic male sterile system has the advantage that fertile hybrid plants can be produced using any normal male fertile line as the male parent. Although removal of the male fertile plants was facilitated greatly by the discovery of a close linkage between genes for genetic male sterility and anthocyanin pigment in the seedling leaves, the high labor cost required to remove the male fertile, anthocyanin pigmented plants from the female rows of seed production field is a disadvantage of the genetic male sterile system. In addition, the requirement to incorporate and maintain the link characters in the female parent is another disadvantage of the genetic male sterile system. P. Leclercq, *Une sterilite male utilisable pour la production d hybrides simples de tournesol*, Ann. Amelior. Plant 16:135–144 (1966).

The system has been replaced largely by the cytoplasmic male sterile and fertility restorer system in most current hybrid sunflower breeding programs. The value of genetic male sterility now appears to be primarily an alternate method of hybrid seed production should problems develop with the use of cytoplasmic male sterility such as occurred in maize with susceptibility to southern corn leaf blight. The system also may have value for developing suitable testers for evaluating inbred lines, and subsequent production of hybrid seed for testing.

Around 1960, the first reports of cytoplasmic sterility indicated that most crosses of cytoplasmic male sterile plants with normal male fertile lines produced progeny with variable percentages of sterile plants. Varying degrees of partial sterility were also reported. Through selection and test crossing, lines that produced 92–96% sterile progeny were developed and utilized in experimental production of hybrid seed. A. I. Gundaev, *Prospects of selection in sunflower for heterosis*, Sb. Rab. Maslichn. Kult., 3:15–21 (1966) and I. A. Gundaev, *Basic principles of sunflower selection*, Genetic Principles of Plant Selection, p. 417–465 (1971). Leclercq in France reported the discovery of cytoplasmic male sterility from an interspecific cross involving *H. petiolaris* Nutt. and *H. annuus* L. This source of cytoplasmic male sterility was shown to be very stable. For more information regarding sunflower breeding and genetics, see Gerhardt N. Fick, *Breeding and Genetics*, Sunflower Science and Technology, pages 279–338 (1978) incorporated herein by reference.

The use of male sterile inbreds is but one factor in the production of sunflower hybrids. The development of sunflower hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_3 \rightarrow F_4$; $F_4 \rightarrow F_5$, etc.

A single cross hybrid sunflower variety is the cross of two inbred lines, each of which has a genotype that complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid sunflower variety involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in sunflower, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Sunflower is an important and valuable field crop. Thus, a continuing goal of plant breeders is to develop high-yielding sunflower hybrids that are agronomically sound based on stable inbred lines. The reasons for this goal are obvious: to maximize the amount of seed produced with the inputs used and minimize susceptibility of the crop to environmental stresses. To accomplish this goal, the sunflower breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

In addition to the preceding problem, it is not known how the genotype will react with the environment. This genotype by environment interaction is an important, yet unpredictable, factor in plant breeding. A breeder of ordinary skill in the art cannot predict the genotype, how that genotype will interact with various environments or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new sunflower inbred line.

SUMMARY OF THE INVENTION

According to the invention, there is provided a novel inbred sunflower line, designated PHA207. This invention thus relates to the seeds of inbred sunflower line PHA207, to the plants of inbred sunflower line PHA207, and to methods for producing a sunflower plant produced by crossing the inbred line PHA207 with itself or another sunflower line. This invention further relates to hybrid sunflower seeds and plants produced by crossing the inbred line PHA207 with another sunflower line.

DEFINITIONS

In the description and examples that follow, a number of terms are used herein. In order to provide a clear and consistent understanding of the specification and claims, including the scope to be given such terms, the following definitions are provided. NOTE: ABS is in absolute terms and %MN is percent of the mean for the experiments in which the inbred or hybrid was grown. These designators will follow the descriptors to denote how the values are to be interpreted. Below are the descriptors used in the data tables included herein.

$/ACR=A calculated trait of the value of oil obtained. Yield (LBS/10) multiplied by the percent oil (OIL10P) multiplied by the average cost paid for sunflower.

50PFLW—The number of days it takes for 50 percent of the plants to reach the stage of R5.1 R5.1 is when the ray flowers are visible and the first ring of disk flowers has emerged and flowered.

BNKSC—A 1 to 9 visual rating indicating the level of neck breakage. The higher the score the less breakage that occurs.

BSKSC—A 1 to 9 visual rating indicating the level of stalk breakage. The higher the score the less breakage that occurs.

CLD TST=COLD TEST. The percent of plants that germinate under cold test conditions.

CTRSET=A 1 to 9 visual rating indicating the degree of seed set obtained within the sunflower head. A 1 equals a head where only the outer 10% of the head sets seed. A 9 equals a head where 90–100% of the head sets seed.

CYTOPLASMIC MALE STERILE (CMS) PLANT OR INBRED LINE. A sunflower line that produces no viable pollen is called male sterile. Male sterility is inherited maternally, i.e. the male sterile plant is used as the female parent in a cross with pollen from another sunflower. CMS lines are produced by crossing a maintainer line with a sunflower plant with the cytoplasmic male sterility trait and then backcrossing to the maintainer line until a male sterile line that is homologous to the maintainer line in all other respects is developed. CMS lines are also referred to as female lines.

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

DNYMLW=A 1 to 9 visual rating indicating the resistance to Downy Mildew (*Plasmopara halstedii*). A higher score indicates greater resistance.

DYSR9=The number of days it takes for 50 percent of the plants to reach the R9 developmental stage. This is a stage of physiological maturity that is determined when the back of the flowering head has reached a yellowing stage and the outer bracts of the head have started to brown. This normally is a stage when the seed moisture is at about 30–40% moisture.

HARHT=This is the height of the head at harvest, measured in decimeters.

HARMST=This is a measure of seed moisture taken at harvest time. It is recorded in percentage of moisture to seed weight.

LBS/10=The grain yield as measured in pounds divided by 10.

OIL10P=The percentage of oil content measured from the harvested grain adjusted to a 10% moisture level.

PHOSC=A 1 to 9 visual rating indicating the resistance to Phompsis stalk rot (*Phompsis helianthii*). A higher score indicates a greater resistance.

PLTHT=This is the height of the head at flowering, measured in decimeters.

PMASC=A 1 to 9 visual rating indicating the resistance to Phoma stalk rot (*Phoma macdonaldii*), The higher score indicates a greater resistance.

R160=A measure of the percentage of Palmitic acid found in the oil of the seed as measured by a rapid reading from a gas chromatograph.

R180=A measure of the percentage of Stearic acid found in the oil of the seed as measured by a rapid reading from a gas chromatograph.

R181=A measure of the percentage of Oleic acid found in the oil of the seed as measured by a rapid reading from a gas chromatograph.

R182=A measure of the percentage of Linoleic acid found in the oil of the seed as measured by a rapid reading from a gas chromatograph.

RESTORER LINE. A line possessing the gene or genes to restore male fertility or viable pollen to a sunflower hybrid or inbred line and progeny having a maternal cytoplasm that conditions male sterility. This term is also discussed in the literature. See for e.g. Fick, "Breeding and Genetics," in Sunflower Science and Technology 279–338 (J. F. Carter ed. 1978), the contents of which are incorporated herein by reference.

RLGSC=A 1 to 9 visual rating indicating the level of root lodging. The higher the score the less root lodging that occurs.

RSTSC=A 1 to 9 visual rating indicating the resistance to Rust (*Puccinia helianthii*). A higher score indicates greater resistance.

SCLHSC=A 1 to 9 visual rating indicating the resistance to Sclerotinia (*Sclerotinia scierotiorum*), head infection. A higher score indicates a greater resistance.

SCLRSC=A 1 to 9 visual rating indicating the resistance to Sclerotinia (*Sclerotinia sclerotiorum*), root and basal stalk infection. A higher score indicates a greater resistance.

SLFFER=A 1 to 9 visual rating indicating the degree of self fertility found within a self pollinated head. A score of 1 indicates <10% of the seed sets under a bagged self. A score of 9 indicates that 90–100% of the seed sets under a bagged self.

STA GRN=STAY GREEN. Stay green is the measure of plant health near the time of black layer formation (physiological maturity). A high score indicates better late-season plant health.

STMCRV=A 1 to 9 visual rating indicating the degree of stem curvature and head attitude. A 1 indicates a very pendulous neck and head whereas a 9 indicates virtually no neck bend and an erect head attitude.

SUNFLOWER SEED. Botanically referred to as an "achene", comprised of the pericarp and embryo.

VERWLT=A 1 to 9 visual rating indicating the resistance to Verticillium wilt (*Verticillium dahliae*). A higher score indicates a greater resistance.

DETAILED DESCRIPTION OF THE INVENTION

Inbred sunflower lines are typically developed for use in the production of hybrid sunflower lines. Inbred sunflower lines need to be highly homogeneous, homozygous and reproducible to be useful as parents of commercial hybrids. There are many analytical methods available to determine the homozygotic and phenotypic stability of these inbred lines.

The oldest and most traditional method of analysis is the observation of phenotypic traits. The data is usually collected in field experiments over the life of the sunflower plants to be examined. Phenotypic characteristics most often observed are for traits associated with plant morphology, flower morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

Inbred sunflower line PHA207 is a excellent male restorer line which is fully branched and has very good genetic combining ability. The inbred has outstanding stay green and lodge rea tion in hybrids. Inbred PHA207 also exhibits Sclerotinia tolerance.

Sclerotinia Disease

Sclerotinia overwinters as dense, black hyphal masses (sclerotia) deposited in the soil. Sclerotia in the soil germinate when favorable conditions are present to produce mycelial growth for root infections or apothecia for above ground ascospore production. Sclerotinia infection in sunflower manifests itself in 4 basic forms; basal root mycelial infection leading to wilt, and middle stock, bud and head rots. Airborne ascospores from soil surface apothecia are responsible for the later three infections. The general view has been that Sclerotinia does not invade healthy tissue but gains a foothold only in wounded areas or senescing tissue where the spores happen to land. This does not appear to be strictly true, however, in that the only correlation to be made for successful ascospore infection in plants is the number of hours of continuous moisture to which spores are exposed during the germination process. Anywhere from 24 to 48 hours of damp conditions as well as some minimal level of plant exudate as a nutritional source are required for spore germination and penetration.

Fungal produced oxalate, in conjunction with a host of degradative enzymes, appears to be a requirement for infection (Noyes, R. D. and J. G. Hancock, *Physiol. Plant Pathol.*, 18(2): 123–132 (1981)). Mutant strains of Sclerotinia deficient in oxalate production are no longer pathogenic even though the battery of degradative enzymes are produced (Godoy, G., et al., *Physiol. Mol. Plant. Pathol.*, 37(3): 179–191 (1990)). In addition, oxalate fed to sunflower plants exhibit the wilt symptoms of Sclerotinia infection. Therefore, oxalate acts as a classic, diffusable toxin by stressing host plant tissue in preparation of enzymatic degradation and mycelial colonization (Maxwell, D. P., *Physiol. Plant Pathol.*, 3(2): 279–288 (1973)).

Tolerant Backgrounds

The combination of a hydrogen peroxide producing enzyme or an oxalate degrading enzyme in a tolerant background yields unexpectedly superior disease resistance compared to the expression of a hydrogen peroxide producing enzyme or an oxalate degrading enzyme in a non-tolerant background. Only in combination do immune or near immune plants result. The sunflower line of the invention exhibits this combination and demonstrates good resistance to Sclerotinia.

In the sunflower case, oxalate oxidase-produced hydrogen peroxide induces the accumulation of factors associated with resistance to stress even though challenges such as pathogen attack are not present. Hydrogen peroxide acts as a signal to induce the expression of genes involved in stress resistance responses resulting in plants that stand ready for various challenges prior to encountering such conditions.

In sunflower, favored spore infection sites are the corollas in the head leading to fungal growth into the fleshy receptacle ultimately destroying the head, the depression at the nodal attachment point of petioles to the main stalk where water can accumulate, and the young inflorescence. Root infections and wilt are more common in dry areas of sunflower production and can occur throughout the plant's life although the seedling stage of infection is most common. Middle stalk and head rots are found in more humid, damp areas and are commonly associated with flowering plants. Thus, tolerant varieties in sunflower can be tolerant in different parts of the plant.

Inbred PHA207 demonstrates Sclerotinia resistance by combining the oxalate degrading enzyme, oxalate oxidase with a Sclerotinia tolerant background resulting in a sunflower inbred line with improved resistance.

The inbred has shown uniformity and stability within the limits of environmental influence for all the traits as described above and in the Variety Description Information (Table 1) that follows. The inbred has been self-pollinated a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in PHA207.

Inbred sunflower line PHA207, being substantially homozygous, can be reproduced by planting seeds of the line, growing the resulting sunflower plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PHA207

Class: Normal  Region Best Adapted: Sunflower growing regions of the U.S.A., Canada, northern and western Europe A. Maturity:

| | |
|---|---|
| Head First Visible (from emergence): | 64 |
| Harvest Ripeness: | 95 |

B. Plant Characteristics:

| | |
|---|---|
| Plant Height: | Tall |
| Plant Type: | Fully branching with Central Head |
| Central Head to Laterals: | above |
| Flowering Height Avd. (cm): | 180 |
| Harvest Height Avg. (cm): | 142 |

TABLE 1-continued

VARIETY DESCRIPTION INFORMATION
INBRED = PHA207

C. Stem:

| | |
|---|---|
| Stem Hair Below Head: | medium |
| Stem Curvature: | strong |
| Hypocotyl Anthocyanin: | strong |

D. Leaves:

| | |
|---|---|
| Blade Length: | 21.0 cm |
| Blade Width: | 20.0 cm |
| Leaf Shape: | cordate |
| Leaf Size: | medium |
| Leaf Apex: | acuminate |
| Leaf Base: | cordate |
| Leaf Serration Coarseness: | coarse |
| Leaf Serration Uniformity: | irregular |
| Leaf Cross Section: | concave |
| Leaf Wings: | absent |
| Leaf Vein Angle: | acut |
| Leaf Angle: | high |
| Leaf Petiole Angle: | small |
| Leaf Wrinkle: | medium |
| Leaf Glossiness: | absent |
| Leaf Margin Anthocyanin: | absent |
| Leaf Color: | green |
| Leaf Number: | medium |
| Leaf Number Average: | 30 |
| Leaf Brow Point Color: | green |
| Leaf Margin Color: | green |
| Comments: | leaves have sharp teeth |

E. Head at Flowering:

| | |
|---|---|
| Flower Date: | very late |
| Ray Flower Numbers: | medium |
| Ray Flower Shape: | elongated |
| Young Bud (at 3 cm Dia): | closed |
| Ray Flower Attitude: | upright |
| Ray Flower Color: | yellow |
| Disk Flower Color: | yellow |
| Anthocyanin in Stigmans: | medium |
| Pollen score: | medium |
| Pollen Color: | yellow |
| Ray Flower Length Avg (min): | 55.0 mm |
| Ray Width: | 16.0 mm |
| Bract Number: | medium |
| Bract Shape: | elongated |
| Bract Anthocyanin: | absent |
| Bract Length (Ave (mm): | 35 |
| Self Fertility: | medium |
| Flower Date: | very late |

F. Head at Seed Maturity:

| | |
|---|---|
| Head Diameter Avg. (cm): | 13.0 cm |
| Seeds Per Head: | 325 |
| Head Shape: | convex |

G. Seeds:

| | |
|---|---|
| Main Color: | black |
| Thickness: | medium |
| Stripes: | none |
| Shape: | ovoid/elongate |
| Seed Width Avg. (mm): | 4 |
| Length Avg. (mm): | 10.0 mm |
| Grams/100 seed | 3.7 gm |
| % Head on 7.9 mm (20/64) Round-Hole Screen | 0.0 |
| Size: | medium |

H. Diseases:

| | |
|---|---|
| Rust: | |
| Verticillium Wilt (V. Dahliae): | |
| Downy Mildew (P. Halstedii): | |
| White Blister Rust (A. Tragopogi): | Not Tested |
| Broom Rape (O. Cumanii): | Not Tested |
| Sclerotinia Wilt (S. Sclerotiorum): | Resistant |
| Leaf Mottle (V. Albo-Atrum): | Not Tested |
| Gray-Mold Blight, Bud Rot (B. Cinerea): | |
| Charcoal Rot, Stem Rot (M. Phaseolina): | Not Tested |
| Macrophomina Phoma: | |
| Alternaria: | |

I. Oil Profile:

| | |
|---|---|
| Palmitic Acid %: | 7 |
| Stearic Acid %: | 3 |
| Oleic Acid %: | 19 |
| Linoleic Acid %: | 72 |

*In interpreting the foregoing color designations, reference may be had to the Munsell Glossy Book of Color, a standard color reference
All data collected from plots in Woodland, California in 1993.

INDUSTRIAL APPLICABILITY

This invention also is directed to methods for producing a sunflower plant by crossing a first parent sunflower plant with a second parent sunflower plant wherein the first or second parent sunflower plant is an inbred sunflower plant of the line PHA207. Further, both first and second parent sunflower plants can come from the inbred sunflower line PHA207. Thus, any such methods using the inbred sunflower line PHA207 are part of this invention: selfing, hybrid production, crosses to populations, and the like. All plants produced using inbred sunflower line PHA207 as a parent are within the scope of this invention. Advantageously, the inbred sunflower line is used in crosses with other, different, sunflower inbreds to produce first generation ($F_1$) sunflower hybrid seeds and plants with superior characteristics.

As used herein, the term plant includes plant cells, plant protoplasts, plant cell tissue cultures from which sunflower plants can be regenerated, plant calli, plant clumps, and plant cells that are intact in plants or parts of plants, such as embryos, pollen, ovules, flowers, leaves, husks, stalks, roots, root tips, anthers, and the like.

Several different methods are used to develop inbred lines depending on such factors as the source populations available and specific program objectives. The most common procedure involves selection of individual plants within open pollinated cultivars or segregating generations of planned crosses.

Although self pollination is used most commonly during the inbreeding process, sib pollinations also may have advantages in developing inbred lines. Aside from theoretical considerations involving the rate of approach to homozygosity, sib matings are especially useful when development or maintenance of lines with a high degree of self incompatibility is desired.

In producing the inbred sunflower of the present invention, parent lines and varieties possessing desirable characteristics may be used to advantage. A preferred line can be obtained, following conventional sunflower breeding by self-pollination for a number of generations, usually three or more, of progeny or of crosses with other lines or varieties, selected for favorable characteristics. Similar breeding methods are described in Fernandez-Martinez, J., et al., Breeding for High Content of Oleic Acid in Sunflower (Helianthus annuus L.) Oil; Helia Nr. Scientific Bulletin of the F.A.O. Research Network on Sunflower 11–15 (1988); Fick, G. N., Sunflower, Oil Crops of the World Ch. 14 pp. 301–318 (1989); Knowles, P. F., Genetics and Breeding of Oil Crops, Oil Crops of the World Ch. 12 pp. 260–282 (1989).

After inbreeding has progressed to the point where progeny are true-breeding for a particular characteristic, the starting material is preferably converted to cytoplasmic male sterility (CMS), in accordance with the present invention, by crossing the selected germplasm with a sunflower line, such as CMS HA89 (U.S. Department of Agriculture), that incorporates a cytoplasmic determinant for male sterility. The source of CMS HA89 and most other currently available CMS lines is from the material of Leclercq, "Cytoplasmic Sterility in the Sunflower," Ann. Amelior. Plant. (French) 19:99–106 (1969).

Inbred lines can also be developed through chromosome duplication of haploids. Author unknown. 1971. "Basic Principles of Sunflower Selection." pp. 417–465. Genetic Principles of Plant Selection. Nauka, Moscow. The main advantage of this method is that pure breeding lines may be developed without several years of inbreeding. The disadvantage is that haploids occur among twin seedlings at a frequency of only 0.64 to 4.76%. Thus, another aspect of this invention is to provide cells which upon growth and differentiation produce sunflower plants having the physiological and morphological characteristics of inbred line PHA207.

Duncan, Williams, Zehr, and Widholm, *Planta*, (1985) 165:322–332 reflects that 97% of maize plants cultured which produced callus were capable of plant regeneration. Subsequent experiments with both inbred and hybrids produced 91% regenerable callus which produced plants. In a further study in 1988, Songstad, Duncan & Widholm in Plant Cell Reports (1988), 7:262–265 reports several media additions which enhance regenerability of callus of two inbred maize lines. Other published reports also indicated that "nontraditional" tissues are capable of producing somatic embryogenesis and plant regeneration, as well as other plant species. For example, regeneration has been shown for dicots as follows: apple, *Malus pumila* (James et al., *Plant Cell Reports* (1989) 7:658); blackberry, Rubus, Blackberry/raspberry hybrid, Rubus, red raspberry, Rubus (Graham et al., *Plant Cell, Tissue and Organ Culture* (1990) 20:35); carrot, *Daucus carota* (Thomas et al., *Plant Cell Reports* (1989) 8:354; Wurtele and Bulka, *Plant Science* (1989) 61:253); rape, *Brassica napus* (Radke et al., *Theor. Appl. Genet.* (1988) 75:685; Moloney et al., *Plant Cell Reports* (1989) 8:238);soybean (wild), *Glycine canescens* (Rech et al., *Plant Cell Reports* (1989) 8:33); and tomato, *Lycopersicon esculentum* (McCormick et al., *Plant Cell Reports* (1986) 5:81);

and examples of monocots include: rice, *Oryza sativa* (Shimamoto et al., *Nature* (1989) 338:274); rye, *Secale cereale* (de la Pena et al., *Nature* (1987) 325:274); and maize, (Rhodes et al., *Science* (1988) 240:204).

In addition regeneration of whole plants from cells (not necessarily transformed) has been observed in: apricot, *Prunus armeniaca* (Pieterse, *Plant Cell Tissue and Organ Culture* (1989) 19:175); asparagus, *Asparagus officinalis* (Elmer et al., *J. Amer. Soc. Hort. Sci.* (1989) 114:1019); Banana, hybrid Musa (Escalant and Teisson, *Plant Cell Reports* (1989) 7:665); and bean, *Phaseolus vulgaris* (McClean and Grafton, *Plant Science* (1989) 60:117). Sunflower regeneration has also been accomplished, See, European Patent Number 486233 and Malone-Schoneberg J.; et. al. *Plant Science* 103 199–207 (1994).

Thus, it is clear from the literature that the state of the art is such that these methods of obtaining plants are, and were, "conventional" in the sense that they are routinely used and have a very high rate of success. Thus, another aspect of this invention is to provide cells which upon growth and differentiation produce sunflower plants having the genotype of PHA207.

Sunflower (*Helianthus annuus*) oil is a major edible oil worldwide. The oil component of sunflower seeds typically contributes about 80 percent of the value of a sunflower crop and is mostly used as a cooking medium. Sunflower oil is also used as salad oil, as well as in the manufacture of margarine, soap, shortening, lubricants, and as a source for biodiesel fuels. In the United States, approximately 1–2 million acres are planted in sunflowers annually, primarily in the Dakotas and Minnesota.

The seed of inbred sunflower line PHA207, the plant produced from the inbred seed, the hybrid sunflower plant produced from the crossing of the inbred, hybrid seed, and various parts of the hybrid sunflower plant can be utilized for human food, livestock feed, and as a raw material in industry.

Performance Examples of PHA207

In the examples that follow, the traits and characteristics of inbred sunflower line PHA207 are given as a line. The data collected on inbred sunflower line PHA207 is presented for the key characteristics and traits.

The results in Table 2A is a T-test comparison of Sunflower inbred PHA207 with a similarly adapted Sunflower inbred, USDA PHA274 for Basal Sclerotinia Resistance. AS can be seen from the table, PHA207 exhibits significantly higher survival rate after challenge with Sclerotinia Head Rot.

TABLE 2A

| YEAR | LOC | EXPID | REP | PHA207 (1X) -percent plants healthy- | RHA274 (X2) | X1-X2 | (X1-X2) |
|---|---|---|---|---|---|---|---|
| 1995 | Woodland, CA | F95HP01 | 1 | 78.0 | 54.0 | 24.0 | 576.00 |
| 1995 | Woodland, CA | F95HP01 | 2 | 36.0 | 58.0 | −22.0 | 484.00 |
| 1995 | Woodland, CA | F95HP01 | 3 | 71.0 | 23.0 | 48.0 | 2304.00 |
| 1995 | Woodland, CA | F95HP01 | 4 | 83.0 | 45.0 | 38.0 | 1444.00 |
| 1997 | Woodland, CA | HP80D307 | 1 | 100.0 | 93.8 | 6.2 | 38.44 |
| 1997 | Woodland, CA | HP80D307 | 2 | 100.0 | 81.8 | 18.2 | 331.24 |
| 1997 | Woodland, CA | HP80D307 | 3 | 94.1 | 80.0 | 14.1 | 198.81 |
| 1997 | Woodland, CA | HP80D307 | 4 | 100.0 | 92.3 | 7.7 | 59.29 |
| 1997 | Woodland, CA | HP80D307 | 5 | 100.0 | 94.1 | 5.9 | 34.81 |
| 1997 | Woodland, CA | HP80D307 | 6 | 93.3 | 92.9 | 0.4 | 0.16 |
| | | | SUM | 855.4 | 714.9 | 140.5 | 5470.75 |
| | | | MEAN | 85.54 | 71.49 | 14.05 | = d |

TABLE 2A-continued

| YEAR | LOC | EXPID | REP | PHA207 (1X) RHA274 (X2) -percent plants healthy- | X1-X2 | (X1-X2) |
|---|---|---|---|---|---|---|

$$SE\ diff = \frac{\sqrt{\Sigma(X1-X2)^2 - (\Sigma X1-X2)^2/n}}{(n)(n-1)}$$

$$SE\ diff = \frac{\sqrt{5470.75 - ((140.5)^2/8)}}{(10)(9)}$$

Ave X1 = 85.54
Ave X2 = 71.49
d = (Ave X1 − Ave X2) = 14.05
n = 10
SE diff = SORT of 38.853
SE diff = 6.233
t = d/SE diff = 2.254
df = 9
Prob > t = 0.051

Basal (Root) Sclerotinia Screening Procedures

The following procedure was used to generate data in Table 2A.

PREPARATION OF SCLEROTINIA INOCULUM

Put oats in large container (i.e. laundry tub, plastic garbage can, etc.), cover with water, allow to soak at room temp for 4 hours. After 4 hours refill with water to replace that which has been soaked up (may soak overnight at this step). One 50 lb. bag of oats will fill quart kettle six times.

Place hydrated oats in stainless steel kettle, cover with lid, cook in autoclave for 1 hour @ 121° C. (takes 2 hours for full cycle). Put kettle in cold room 4 hours to overnight to cool enough to handle. One 50 lb. bag of oats will fill quart kettle about 6 times.

Prep for Mason jars. Get wide-mouth, quart or half-gallon Mason jars. Drill ¾" hole in center. Run jars through dishwasher prior to use. Insert sponge rubber stopper (SP#T1385) in hole in lid.

Fill Mason jars ¾ full of cooked oats, add 25 ml. water to quarts. Or 50 ml. to half-gallon jars. Two kettle loads of cooked oats will fill 40–45 half-gallon jars, but only 20–25 half-gallon jars will fit in autoclave at one time. Quart jars can be stacked two high if necessary. Autoclave for 1 hour for quart jars, 1 hour 30 minutes for half-gallon jars, cool S-L-O-W-L-Y, so jars don't break.

Let sit 36–48 hours (this allows any bacteria which were not killed in the first autoclaving to germinate and be killed in the second autoclaving.)

After jars thoroughly cooled (preferably overnight), inoculate them with 3–4 pieces of actively growing PDA culture of Sclerotinia (takes 3–5 days to get growth over entire plate). One petri dish will inoculate 12–15 jars. Do this in transfer hood. Start cultures from sclerotia regularly. (Soak sclerotia in 20% bleach for 5 minutes, cut in half to speed germination.) If you keep transferring Sclerotinia the culture may loose pathogenicity.

Place jars back in boxes, and put in storeroom at 18–20° C. (65–68° F.), adjust thermostat accordingly. Check on jars weekly. Discard any which smell bad or look contaminated. Reinoculate any that don't start to show growth in 2–3 days. If jars are laid on their sides, they may grow faster. Also, shaking up oats during the first week will help distribute the mycelium and make it grow faster.

After 3–4 weeks (by which time mycelium will have reached bottom of jar and some sclerotia will be forming on surface of oats), dump out jars on drying racks (we prepared previously for drying scloerotia) and air-dry thoroughly for several days. Don't rise temperature above 80–90° F., and keep air volume low. Dried inoculum can be packaged in plastic bags, sealed tightly, and stored in the cold room.

INOCULATION PROCEDURE

For inoculation, weigh (measure) out approximately 7 ml. of oats/sclerotia and place in small coin envelope.

Using a jab planter, place inoculum about 2" away from stem about 1–2 week prior to flowering.

To reduce experimental error all entries with replication are inoculated by the same person.

SCORING PROCEDURES

A count of the number of total inoculated plants in the row is taken two to three weeks after the plants are inoculated. Readings are then taken 10–12 days thereafter for two to four weeks. The number of healthy plants are counted. Plants are counted as being healthy until almost all of the leaves are wilted. A plant with only a few leaves or a little wilting is considered healthy. If the Sclerotinia basal stalk rot infection is indeed progressing in the plant, wilting will continue and the plant will be not counted in one of the next readings as healthy. Under ideal conditions, this test can be quite severe. Therefore readings are taken over time. Those readings where best differentiation occurred are included in this patent application.

Reference: M. L. Mancl and S. E. Shein 1982: pg. 167, *Field Inoculation of Sunflower for SCLEROTINIA SCLEROTIORUM Basal Stalk Rot and Virulence of Isolates from Various Hosts*; 10$^{th}$ International Sunflower Conference, Surfers Paradise, Australia, Mar. 14–18, 1982.

Deposits

Applicant has made a deposit of at least 2500 seeds of Inbred Sunflower Line PHA207 with the American Type Culture Collection (ATCC), Manassas, Va. 20110 USA, ATCC Deposit No. PTA-893. The seeds deposited with the ATCC on Oct. 29, 1999 were taken from the deposit maintained by Pioneer Hi-Bred International, Inc., 800 Capital Square, 400 Locust Street, Des Moines, Iowa 50309-2340 since prior to the filing date of this application. This deposit of the Inbred Sunflower Line PHA207 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801–1.809, including providing an indication of the viability of the sample.

Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or of rights which may accure under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

What is claimed is:

1. Seed of sunflower inbred line designated PHA207, representative samples having been deposited under ATCC Accession No. PTA-893.

2. A sunflower plant, or parts thereof, having all the physiological and morphological characteristics of inbred line PHA207, representative seed of said line having been deposited under ATCC accession No. PTA-893.

3. The sunflower plant of claim 2, wherein said plant is cytoplasmically male sterile.

4. A tissue culture of regenerable cells of a sunflower plant of inbred line PHA207, representative seed of which have been deposited under ATCC Accession No. PTA-893, wherein the tissue regenerates plants capable of expressing all the morphological and physiological characteristics of the inbred line PHA207.

5. A tissue culture according to claim 4, the cells or protoplasts being of a tissue selected from the group consisting of leaves, pollen, embryos, roots, root tips, anthers, flowers and stalks.

6. A sunflower plant regenerated from the tissue culture of claim 4, capable of expressing all the morphological and physiological characteristics of inbred line PHA207, representative seed of which have been deposited under ATCC Accession No. PTA-893.

7. A method for producing a first generation ($F_1$) hybrid sunflower seed comprising crossing the plant of claim 2 with a different inbred parent sunflower plant and harvesting the resultant first generation ($F_1$) hybrid sunflower seed.

8. The method of claim 7 wherein inbred sunflower plant of claim 2 is the female or male parent.

9. An $F_1$ hybrid seed produced by crossing the inbred sunflower plant according to claim 2 with another, different sunflower plant.

10. An $F_1$ hybrid plant, or parts thereof, grown from the seed of claim 9.

11. The sunflower plant of claim 2, wherein said plant exhibits Basal Sclerotinia Resistance.

* * * * *

UNITED STATES PATENT AND TRADEMARK OFFICE
CERTIFICATE OF CORRECTION

PATENT NO. : 6,166,305  
DATED : December 26, 2000  
INVENTOR(S) : Carlos Martino Page 1 of 1

It is certified that error appears in the above-identified patent and that said Letters Patent is hereby corrected as shown below:

<u>Column 14,</u>  
Line 51, underline the heading "Deposits".  
Line 54, delete "Va." and insert -- VA --.

<u>Column 15,</u>  
Line 7, delete "accure" and insert -- accrue --.  
Between lines 17 and 18, insert the heading -- <u>Claims</u> --.

Signed and Sealed this

Twenty-fifth Day of December, 2001

JAMES E. ROGAN  
*Director of the United States Patent and Trademark Office*

*Attest:*

*Attesting Officer*